(12) United States Patent
Noonan et al.

(10) Patent No.: US 11,690,975 B2
(45) Date of Patent: Jul. 4, 2023

(54) HUB FOR DEVICE NAVIGATION WITH OPTICAL SHAPE SENSED GUIDEWIRE

(71) Applicant: KONINKLIJKE PHILIPS N.V., Eindhoven (NL)

(72) Inventors: David Paul Noonan, New York, NY (US); Molly Lara Flexman, Melrose, MA (US); Aryeh Leib Reinstein, Bronx, NY (US); Neriman Nicoletta Kahya, Eindhoven (NL); Martinus Bernardus Van Der Mark, Best (NL); Sander Hans Denissen, Best (NL); Eibert Gerjan Van Putten, 's-Hertogenbosch (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1454 days.

(21) Appl. No.: 15/763,143

(22) PCT Filed: Oct. 2, 2016

(86) PCT No.: PCT/EP2016/073529
§ 371 (c)(1),
(2) Date: Mar. 26, 2018

(87) PCT Pub. No.: WO2017/055620
PCT Pub. Date: Apr. 6, 2017

(65) Prior Publication Data
US 2018/0279909 A1    Oct. 4, 2018

Related U.S. Application Data

(60) Provisional application No. 62/349,298, filed on Jun. 13, 2016, provisional application No. 62/236,172, filed on Oct. 2, 2015.

(51) Int. Cl.
*A61M 25/00* (2006.01)
*A61B 5/06* (2006.01)
(Continued)

(52) U.S. Cl.
CPC ......... *A61M 25/0097* (2013.01); *A61B 5/064* (2013.01); *A61B 5/065* (2013.01);
(Continued)

(58) Field of Classification Search
CPC .. G02B 6/3684; G02B 6/3696; G02B 6/2835; G02B 6/2856; A61M 1/156; A61M 5/14232; A61M 39/288; A61M 39/284
See application file for complete search history.

(56) References Cited

U.S. PATENT DOCUMENTS

| 136,309 | A | * | 2/1873 | Day | A61M 39/284 251/9 |
| 2,366,424 | A | * | 1/1945 | Perry | A61M 39/284 251/8 |

(Continued)

FOREIGN PATENT DOCUMENTS

| JP | 2014124302 A | * | 7/2014 | A61B 5/065 |
| JP | 2014124302 A | | 7/2014 | |

(Continued)

*Primary Examiner* — Katherine H Schwiker
*Assistant Examiner* — Adam J. Cermak

(57) ABSTRACT

A hub for an optical shape sensing reference includes a hub body (606) configured to receive an elongated flexible instrument (622) with a shape sensing system coupled to the flexible instrument within a path formed in the hub body. A profile (630) is formed in the hub body in the path to impart a hub template configured to distinguish a portion of the elongated flexible instrument within the hub in shape sensing data. An attachment mechanism (616) is formed on the hub body to detachably connect the hub body to a deployable instrument such that a change in a position of the hub (Continued)

body indicates a corresponding change in the deployable device.

13 Claims, 14 Drawing Sheets

(51) Int. Cl.
    *A61B 90/00*     (2016.01)
    *A61B 34/20*     (2016.01)
    *A61M 25/10*     (2013.01)
    *G02B 6/38*     (2006.01)
    *A61M 39/10*     (2006.01)
    *A61M 39/06*     (2006.01)
    *G01B 11/16*     (2006.01)
    *G01B 11/24*     (2006.01)

(52) U.S. Cl.
    CPC .............. *A61B 90/37* (2016.02); *G01B 11/18* (2013.01); *G01B 11/24* (2013.01); *A61B 5/066* (2013.01); *A61B 2034/2061* (2016.02); *A61M 25/0023* (2013.01); *A61M 25/0074* (2013.01); *A61M 25/1002* (2013.01); *A61M 39/06* (2013.01); *A61M 39/10* (2013.01); *G02B 6/3897* (2013.01)

(56) References Cited

U.S. PATENT DOCUMENTS

| | | | | |
|---|---|---|---|---|
| 3,822,052 | A * | 7/1974 | Lange | A61B 17/122 251/10 |
| 4,477,725 | A * | 10/1984 | Asawa | G01L 1/245 250/231.19 |
| 4,643,389 | A * | 2/1987 | Elson | A61M 39/284 251/10 |
| 5,195,162 | A * | 3/1993 | Sultan | G01D 5/268 356/615 |
| 5,258,614 | A * | 11/1993 | Kidwell | G01L 19/0092 374/E11.015 |
| 5,818,982 | A * | 10/1998 | Voss | G02B 6/14 385/13 |
| 6,429,421 | B1 * | 8/2002 | Meller | G02B 6/3628 73/818 |
| 6,592,544 | B1 * | 7/2003 | Mooney | A61M 39/24 604/35 |
| 6,983,096 | B2 * | 1/2006 | Pacheco | G02B 6/24 385/136 |
| 10,492,871 | B2 * | 12/2019 | Blumenkranz | A61B 1/00165 |
| 10,639,007 | B2 * | 5/2020 | Cole | A61B 34/20 |
| 11,191,593 | B2 * | 12/2021 | Flexman | A61B 34/20 |
| 2004/0163809 | A1 * | 8/2004 | Mayeu | E21B 47/09 166/334.1 |
| 2005/0025647 | A1 * | 2/2005 | Ortega | F04B 43/1253 417/477.1 |
| 2005/0063662 | A1 * | 3/2005 | Carpenter | G02B 6/3636 385/136 |
| 2006/0015074 | A1 * | 1/2006 | Lynn | A61M 39/284 604/267 |
| 2007/0299423 | A1 * | 12/2007 | Jones | A61F 2/013 604/523 |
| 2008/0147001 | A1 | 6/2008 | Al-Marashi et al. | |
| 2009/0137952 | A1 * | 5/2009 | Ramamurthy | A61B 5/06 604/95.01 |
| 2010/0202733 | A1 * | 8/2010 | Herden | H01S 5/4025 372/50.12 |
| 2011/0113852 | A1 * | 5/2011 | Prisco | A61B 34/30 385/13 |
| 2011/0202069 | A1 * | 8/2011 | Prisco | A61B 17/24 606/1 |
| 2012/0289777 | A1 * | 11/2012 | Chopra | A61B 1/000094 382/128 |
| 2013/0028554 | A1 * | 1/2013 | Wong | A61B 1/009 385/12 |
| 2013/0276557 | A1 * | 10/2013 | Duindam | A61B 34/37 73/865.8 |
| 2014/0060655 | A1 * | 3/2014 | Ramos | F16K 7/063 251/9 |
| 2014/0275997 | A1 * | 9/2014 | Chopra | A61B 34/30 600/424 |
| 2015/0031987 | A1 * | 1/2015 | Pameijer | A61M 25/0105 600/424 |
| 2016/0213432 | A1 * | 7/2016 | Flexman | A61B 5/065 |
| 2017/0215973 | A1 * | 8/2017 | Flexman | A61B 34/20 |
| 2018/0014886 | A1 * | 1/2018 | Flexman | A61B 5/6851 |
| 2018/0279909 | A1 * | 10/2018 | Noonan | A61M 25/0097 |
| 2019/0000562 | A1 * | 1/2019 | Thienphrapa | A61B 34/20 |
| 2019/0167357 | A1 * | 6/2019 | Noonan | A61B 34/20 |

FOREIGN PATENT DOCUMENTS

| | | | | |
|---|---|---|---|---|
| WO | WO-9840774 | A1 * | 9/1998 | ........... G02B 6/3805 |
| WO | WO-0133165 | A1 * | 5/2001 | ............... A61B 5/06 |
| WO | WO-2013024418 | A1 * | 2/2013 | ........ A61B 1/00147 |
| WO | WO-2014053934 | A1 * | 4/2014 | ............. A61B 34/20 |
| WO | 2014191871 | A1 | 12/2014 | |
| WO | WO-2014191871 | A1 * | 12/2014 | ............. A61B 5/065 |

* cited by examiner

HUB FOR DEVICE NAVIGATION WITH OPTICAL SHAPE SENSED GUIDEWIRE

CROSS-REFERENCE TO PRIOR APPLICATIONS

This application is the U.S. National Phase application under 35 U.S.C. § 371 of International Application Serial No. PCT/EP2016/073529, filed on Oct. 2, 2016, which claims the benefit of U.S. Patent Application No. 62/349,298, filed on Jun. 13, 2016 and U.S. Patent Application No. 62/236,172, filed on Oct. 2, 2015. These applications are hereby incorporated by reference herein.

RELATED APPLICATION DATA

The present application claims the benefit under 35 U.S.C. § 119 to U.S. Provisional Patent Application Ser. No. 62/236,172, filed on Oct. 2, 2015 and U.S. Provisional Patent Application Ser. No. 62/349,298, filed on Jun. 13, 2016, the contents of which are incorporated herein by reference as though set forth in full.

BACKGROUND

Technical Field

This disclosure relates to medical instruments and more particularly to shape sensing optical fibers in guidewires configured to conform to a profile in a hub for device navigation in medical applications.

Description of the Related Art

A medical device such as a catheter, deployment system, or sheath can be enabled with shape sensing by embedding an optical fiber(s) within the device. This requires customizing a mechanical design of the device to add an additional lumen for the fiber. Adding the fiber also adds cost to the device and necessitates the use of an additional shape sensing system. Such devices are known as 'over-the-wire' devices as they are typically used in conjunction with a guidewire that travels through a lumen in the device.

Optical shape sensing (OSS) or Fiber-Optical RealShape™ (also known as "Optical Shape Sensing", "Fiber Shape Sensing", "Fiber Optical 3D Shape Sensing", "Fiber Optic Shape Sensing and Localization" or the like) employs light along an optical fiber for device localization and navigation during surgical intervention. One principle involved makes use of distributed strain measurement in the optical fiber using characteristic Rayleigh backscatter or controlled grating patterns. Multiple optical fibers can be used together to reconstruct a 3D shape, or a single optical fiber with multiple cores that may also be helixed for a lower-profile sensor. The shape along the optical fiber begins at a specific point along the sensor, known as the launch or z=0, and the subsequent shape position and orientation are relative to that point. Optical shape sensing fibers can be integrated into medical devices to provide live guidance of the devices during minimally invasive procedures.

SUMMARY

In accordance with the present principles, a hub for an optical shape sensing reference includes a hub body configured to receive an elongated flexible instrument with a shape sensing system coupled to the flexible instrument within a path formed in the hub body. A profile is formed in the hub body in the path to impart a hub template configured to distinguish a portion of the elongated flexible instrument within the hub body in shape sensing data. An attachment mechanism is formed on the hub body to detachably connect the hub body to a deployable instrument such that a change in a position of the hub body indicates a corresponding change in the deployable device.

A system for an optical shape sensing includes a hub body configured to receive an elongated flexible instrument with an optical shape sensing system coupled to the flexible instrument within a path formed in the hub body. A profile is formed in the hub body in the path to impart a hub template configured to distinguish a portion of the elongated flexible instrument within the hub in shape sensing data. An attachment mechanism is formed on the hub body to detachably connect the hub body to a deployable instrument. An optical sensing module is coupled to the optical shape sensing system to interpret the shape sensing data to identify the hub template in the shape sensing data to account for a position of the hub and the deployable instrument during deployment in a medical procedure.

Another system for an optical shape sensing includes a hub body configured to receive an elongated flexible instrument with an optical shape sensing system coupled to the flexible instrument within a deformable path formed in the hub body. The deformable path includes a mechanism for displacing the flexible instrument to form a profile in the hub body in the deformable path to impart a hub template, when the mechanism is in a first position, to distinguish a portion of the elongated flexible instrument within the hub in shape sensing data. An attachment mechanism is formed on the hub body to detachably connect the hub body to a deployable instrument.

Another hub for an optical shape sensing reference includes a hub body configured to receive an elongated flexible instrument with a shape sensing system coupled to the flexible instrument within a path formed in the hub body. A deformable mechanism is associated with the hub body and configured to move between at least two positions, wherein at least one of the at least two positions generates a template position configured to distinguish a portion of the elongated flexible instrument within the hub body in shape sensing data.

A hub system for an optical shape sensing reference includes a hub body configured to receive an elongated flexible instrument with a shape sensing system coupled to the flexible instrument within a path formed in the hub body. A deformable mechanism is associated with the hub body and configured to move between at least two positions, wherein at least one of the at least two positions generates a template configuration configured to distinguish a portion of the elongated flexible instrument within the hub body in shape sensing data. An optical sensing module is coupled to the optical shape sensing system to interpret the shape sensing data to identify the template position against stored templates to identify a position of the hub on the flexible instrument.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein:

FIGS. 12A, 12B, 12C and 12D is a transparent side view showing a hub with a lever mechanism in an engaged position and in an unengaged position to adjust a shape sensed flexible instrument in accordance with another embodiment;

DETAILED DESCRIPTION OF EMBODIMENTS

Figure 1:
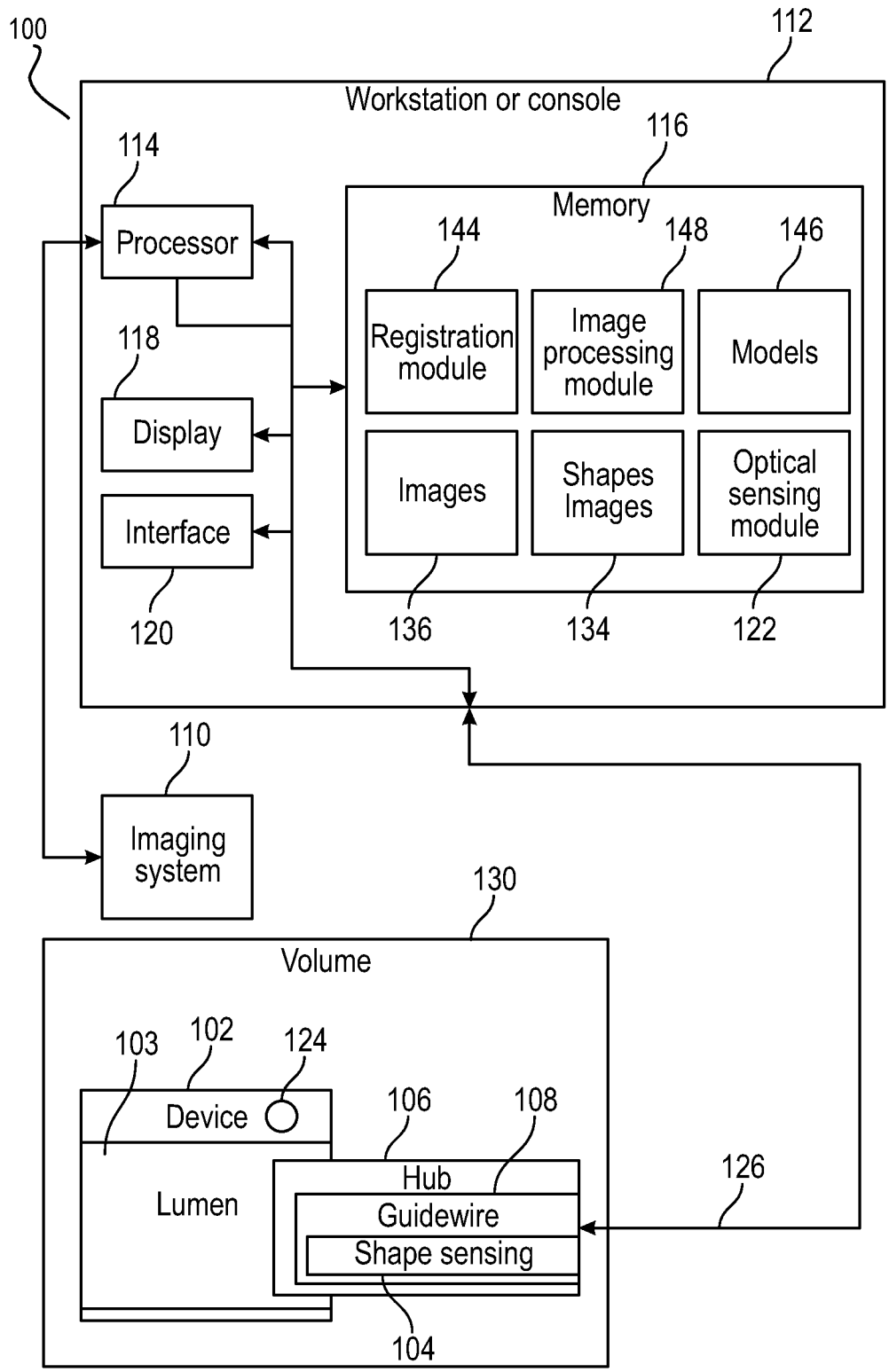
FIG. 1 is a block/flow diagram showing a shape sensing hub for inferring a position/orientation of a deployable device in accordance with one embodiment.

In accordance with the present principles, a shape sensed guidewire is provided for use in a lumen that also senses the position of any commercial over-the-wire device or component. If a catheter (or other deployable device) is employed over a shape sensed guidewire (or other flexible elongated device) then the guidewire shape also defines the catheter shape for the length over which the catheter overlaps the guidewire. To properly define the position of the catheter along the guidewire, a relationship between the catheter and the guidewire needs to be known. This can be done by using a hub device to cause the guidewire to take on a specific shape, curvature, or strain profile (shape profile) at a specific position along the catheter. A method to induce such a shape, curvature or strain profile is to employ the 'hub' with a known profile which can be stored as a template.

When a shape sensed device is inside a non-shape sensed device, the shape information from the sensed device can be used to infer information about the shape and position of the unsensed device. The registration needed may include a longitudinal translation between the two devices. This registration can be performed by using a known shape deformation of the sensed device at a specific location along the unsensed device. The shape deformation can be detected through curvature detection, axial strain (from heating or tensions), 2D or 3D shape matching, etc.

Multiple different versions of hub designs may be employed. In the case of hubs that use a shape deformation (as opposed to a strain deformation due to temperature, for example), the shape deformation will also define a plane. The same hub device can be used to track orientation of the device (e.g., roll about its longitudinal axis). Orientation of the hub at a proximal part of the device may map 1-to-1 to a therapeutic such as a balloon, valve, endograft, stent, etc. located in the distal portion.

The present principles describe hub designs that can be used to create a template profile. These designs may include, e.g., a Luer lock hub, an over-catheter hub, a hemostatic valve hub, among others. A hub may be defined as a component that can create a shape or curvature deformation in a shape sensed device, such as a guidewire. Such a component should be able to work in a wide range of commercially available medical devices within a clinical environment. The hub design can be employed across multiple device designs. Multiple different versions of hub designs can be used for deforming the guidewire and performing longitudinal encoding.

Once the position and orientation of the over-the-wire device is known, it can be employed to display a model of a therapeutic such as a balloon, valve, endograft, stent, etc. In endovascular aneurysm repair (EVAR), the position of the endograft needs to be known so that other catheters and endografts can be navigated with respect to an original endograft. This calls for significant amounts of fluoroscopy and contrast. If the endografts are not correctly positioned, a number of issues may arise.

EVAR replaced open surgery as the most common technique for the repair of abdominal aortic aneurysms (AAA). The procedure is usually carried out under x-ray fluoroscopy guidance and uses significant amounts of contrast to position and deploy the stent graft correctly. On average 50-100 mL of contrast dye is used during an EVAR procedure, which can result in acute renal failure in ~7% of cases. One complication from EVAR is endoleaks resulting from an insufficient seal of the stent graft to the aorta. Endoleaks involve incorrect flow around the stent (for example, flow around the stent at the proximal or distal attachment site, flow through the graft wall, retrograde flow from the branches, etc.). Another complication of EVAR involves ischemia of the aortic side branches (such as the colonic, renal, and pelvic arteries). This can occur due to misplacement of the stent graft such that the stent partially or completely covers one of the side vessels, and this is associated with a lack of high-quality imaging technology as well as the learning curve of the endovascular team.

In EVAR, stent grafts are contained within a stent-deployment system that is used to navigate the stent to the correct part of the vasculature. The deployment systems tend to be relatively large and stiff endovascular devices. They typically involve a handle or set of knobs and dials at the proximal end to control the various steps around the stent deployment. The stent lies within the distal part of the device and is only released once the device has been navigated to the appropriate location. In some cases the stent completely deploys in one step, while in other cases the stent can be partially deployed to allow for correct positioning and orientation before the final deployment step firmly attaches the stent to the vasculature (typically through the retaining/sealing ring).

The endovascular stent graft needs a sufficient amount of healthy vasculature where it can land its sealing ring. If this is not possible beneath the renal arteries, then the stent will cover those arteries, and needs to create some alternative way of maintaining flow to those vessels. This can be done with a fenestrated stent (e.g., a stent with windows for the side-branches) in a procedure known as fenestrated endovascular aneurysm repair (FEVAR). In this case, the stent has fenestrations that are lined up correctly with the side branches and additional stents are placed to connect the side vessels to the main stent.

Under x-ray guidance the stent can be visualized through x-ray visible markers that are located in key positions on the stent. In the fenestrated stent, the markers identify the locations of the fenestrations and can be used to orient the stent to appropriately align the fenestrations with the side vessels.

In accordance with the present principles, devices and methods include registering a hub to a target node of an over-the-wire device and visualizing the over-the-wire device and a model at a target node in the over-the-wire device. This permits any commercial catheter, deployment system, sheath, or other such device to be navigated using a shape sensed guidewire. In useful embodiments, devices and methods make use of a proximal hub to determine orientation of a distal portion of a device such as a commercially available catheter, deployment system, or sheath that is fitted over a shape sensing guidewire. The hub may include a shape profile that deflects the guidewire passing through it into a known shape. That shape can be detected along the fiber to know the longitudinal registration between the guidewire and the over-the-wire device. Since the hub is coupled to the over-the-wire device, the hub shape can also be used to track the rotation or position applied to the proximal part of the over-the-wire device.

In one embodiment, the rotation of the hub (and hence the entire device) can be measured by fitting a plane to the known shape profile inside the hub, and tracking the orientation of that plane over time. In one embodiment, a model of a fenestrated endograft is rotated to better align the fenestrations on the endograft with an anatomical model. The rotation of the hub shape about itself is used to map the rotation of the endograft that is housed within a distal portion of the device. This allows any commercial catheter (manual or robotic), deployment system, sheath, or other such device to be navigated using a shape sensed guidewire. This can be applied to many applications such as vascular (catheters, sheaths, deployment systems, etc.), endoluminal (endoscopes), orthopedic (k-wires & screwdrivers) as well as non-medical applications.

To provide a more efficient registration, a deformable registration device utilizing Fiber-Optical RealShape™ (FORS™ also known as "Optical Shape Sensing", "Fiber Shape Sensing", "Fiber Optical 3D Shape Sensing", "Fiber Optic Shape Sensing and Localization" or the like) may be used. A Fiber-Optical RealShape™ system is a commercial name for systems developed by Koninklijke Philips, N.V. As used herein, the terms FORS™ and FORS™ systems are not, however, limited to products and systems of Koninklijke Philips, N.V., but refer generally to fiber optic shape sensing and fiber optic shape sensing systems, fiber optic 3D shape sensing, fiber optic 3D shape sensing systems, fiber optic shape sensing and localization and similar technologies.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems and procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, a system 100 for monitoring shape sensing enabled devices and other devices is illustratively shown in accordance with one embodiment. System 100 may include a workstation 112 (or console) from which a procedure is supervised and/or managed. Workstation 112 preferably includes one or more processors 114 and memory 116 for storing programs and applications. Memory 116 may store an optical sensing module 122 configured to interpret optical feedback signals from a shape sensing device or system 104 (FORS™). Optical sensing module 122 is configured to use the optical signal feedback (and any other feedback) to reconstruct deformations, deflections and other changes associated with shape sensed devices. In accordance with the present principles, a medical device 102 (alternatively "instrument") comprises a lumen 103, which receives a guidewire 108 or other elongated flexible instrument therein. The guidewire 108 is configured to receive the shape sensing system 104 therethrough. The medical device 102 may include a catheter, a sheath, a probe, an endoscope, a robot, an electrode, a filter device, a balloon device, a graft, a stent or other medical component having a lumen, etc. The medical device 102 is considered to be an over-the-wire device or component. The medical device 102 includes a hub 106 that may be configured within the medical device 102, applied (connected/coupled) to the medical device 102 or configured to fit within the medical device 102.

The shape sensing system 104 includes one or more optical fibers which may be arranged in a set pattern or patterns. The optical fibers 126 connect to the workstation 112 through cabling. The cabling may include fiber optics, electrical connections, other instrumentation, etc., as needed.

Shape sensing system 104 with fiber optics may be based on fiber optic Bragg grating sensors, Rayleigh scattering, or other types of scattering. Inherent backscatter in conventional optical fiber can be exploited, such as Raleigh, Raman, Brillouin or fluorescence scattering. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, or in multiple single-core fibers arranged together, the 3D shape and dynamics of the surface of interest can be followed.

A fiber optic Bragg grating (FBG) system may also be employed for shape sensing system 104. FBG is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

Fresnel reflection at each of the interfaces where the refractive index is changing is measured. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors.

Incorporating three or more cores permits a three dimensional form of such a structure to be precisely determined. From the strain measurement, the curvature of the structure can be inferred at that position. From the multitude of measured positions, the total three-dimensional form is determined. A similar technique can be used for multiple single-core fibers configured in a known structure or geometry.

In one embodiment, workstation 112 is configured to receive feedback from the shape sensing system 104 and record accumulated position data as to where the shape sensing system 104 has been within a volume 130. The shape sensing information within the space or volume 130 can be displayed on a display device 118. Workstation 112 includes the display device 118 for viewing internal images of a subject (patient) or volume 130 and may include shape images 134 as an overlay on medical images 136 such as x-ray images, computed tomography (CT) images, magnetic resonance images (MRI), real-time internal video images or other images as collected by an imaging system 110 in advance or concurrently. Display device 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

A registration device 144 is stored in memory 116 and is configured to register the hub 106 to a target node(s) 124 in the over-the-wire medical device 102. The target node 124 may include any identifying features on the medical device 102 that can be employed as a reference for the hub 106. The medical device 102 and the target node 124 are preferably visualized in an image or medical images 136. In addition, a virtual model 146 of the over-the-wire medical device 102 may be rendered using the target node 124 as a reference to visualize in the over-the-wire medical device 102.

In one embodiment, the hub 106 is registered to the target node 124 in the over-the-wire medical device 102 by attaching the hub 106 to a proximal portion of an over-the-wire medical device 102 to enable a registration (e.g., longitudinal) between the shape sensed guidewire 108 and the over-the-wire medical device 102. To create a meaningful visualization of the over-the-wire medical device 102, the hub location may be mapped to other device nodes. Target nodes 124 are considered to be device features of interest to the clinician. Examples may include a device tip, a position of a fenestration, start and end points of a balloon, location of an ultrasound transducer, etc.

In one embodiment, the target node 124 may include a tip position of the medical device 102. This target node 124 may be employed for positioning many devices and may be employed for safety reasons (e.g., making sure that the tip does not protrude too far into certain vessels that the tip of the device remains inside the vessel, etc.). When the hub 106 is attached to the over-the-wire medical device 102, it is not possible to correctly visualize the device in space until the mapping between the tip of the medical device 102 and the hub 106 is known.

This mapping can be done in a plurality of ways. For example, a length of the medical device 102 may be input to an image processing module 148, which renders a position and dimension(s) of the devices using visualization software. This may be provided by scanning a barcode of the medical device 102 and looking up its properties in a database, the user entering a value directly or reading values from a device package, measuring by hand, etc. In another embodiment, the medical device 102 may be recognized by the image processing module 148 using an x-ray image and automatically looking up the information from a database. In another embodiment, the medical device 102 may be placed and attached to the hub 106 in an x-ray field of view (FOV) and have its length/dimension automatically detected from the resulting image.

This can be done by automatically detecting the device tip in the x-ray image or having the user click on the device tip in an image using e.g., a mouse (interface 120). One or more x-ray projections can be employed, and this can work for all devices. In addition, automatic detection may be performed in other ways, e.g., to know the length, just align the guidewire tip with the tip of the device and click a button, or, loop the tip of the device back onto a known feature on the hub (a divot, for example) and click a button.

In accordance with the present principles, hub 106 provides a straightforward attachment onto a wide range of commercial devices. The function of the guidewire 108 is preserved, e.g., for clinical manipulation such as translation and torqueing. The hub 106 provides an integrated solution for the transfer of data (e.g., hub templates, etc.). The hub 106 is employed to create shape deformation in the guidewire 108 that can be used for longitudinal registration. The hub 106 preferably can be retrofit to any commercial medical device (102) that runs over a guidewire 108 (or other elongated flexible shape sensed device). For example, the medical device 102 may include a catheter, sheath, introducer, endograft deployment system, valve deployment system, transseptal needle, etc. These devices have a wide range of sizes, flexibility and profiles.

Figure 2A:
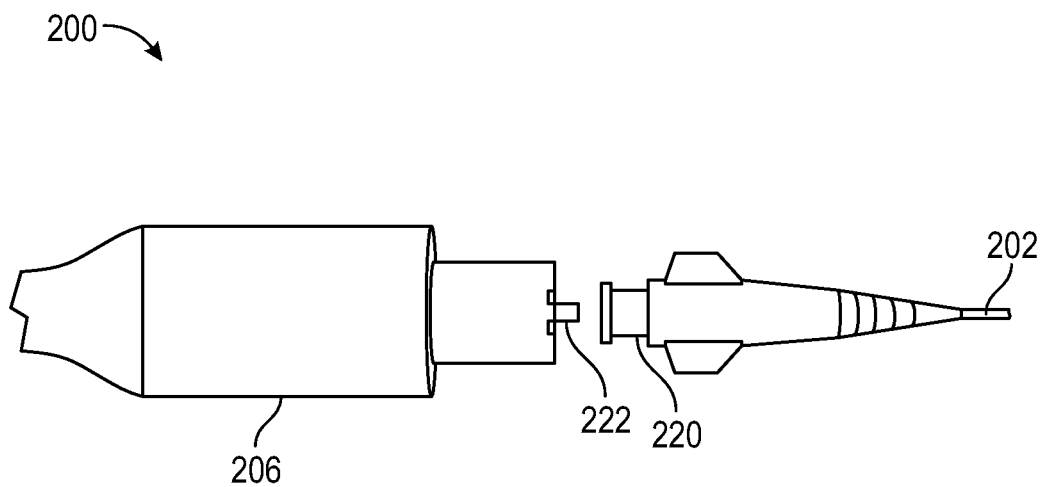
FIGS. 2A and 2B shows images and a schematic diagram of a hub having a Luer lock attachment feature in accordance with one embodiment.
Figure 2B:
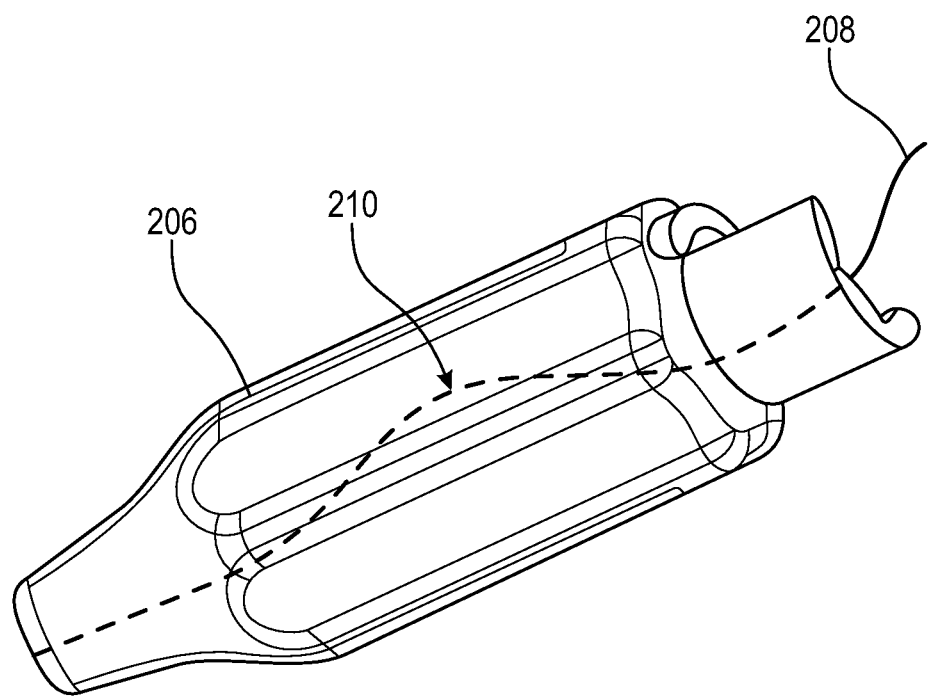

Referring to FIGS. 2A and 2B, a cylindrical Luer lock hub 206 (hereinafter "hub") deforms a guidewire 208 into a known shape profile 210. The guidewire 208 includes a lumen for receiving a FORS™ system, and the guidewire 208 can pass through a lumen into a catheter 202 (medical device 102). Many devices include a male Luer lock component 220 at a proximal end of the guidewire lumen in the catheter 202. This male Luer lock component 220 is used to flush the device with saline prior to use, or to flush with contrast during use. The hub 206 has a female Luer lock 222 on its distal portion which can mate onto the proximal end of the catheter 202. This effectively extends the guidewire lumen, and the extended portion is employed to create a known curvature change. An additional advantage of using a Luer lock system 200 is that clinicians are already familiar with how to use it, and it would not hinder workflow. In one embodiment, a secondary attachment or lock may be employed that can lock the hub 206 onto the catheter 202 so that during torqueing the hub does not decouple from the catheter 202. The attachment (secondary lock 232 in FIG. 3) will catch the catheter 202 lock for torqueing in one direction, but will permit it to loosen in the other direction.

Figure 3:
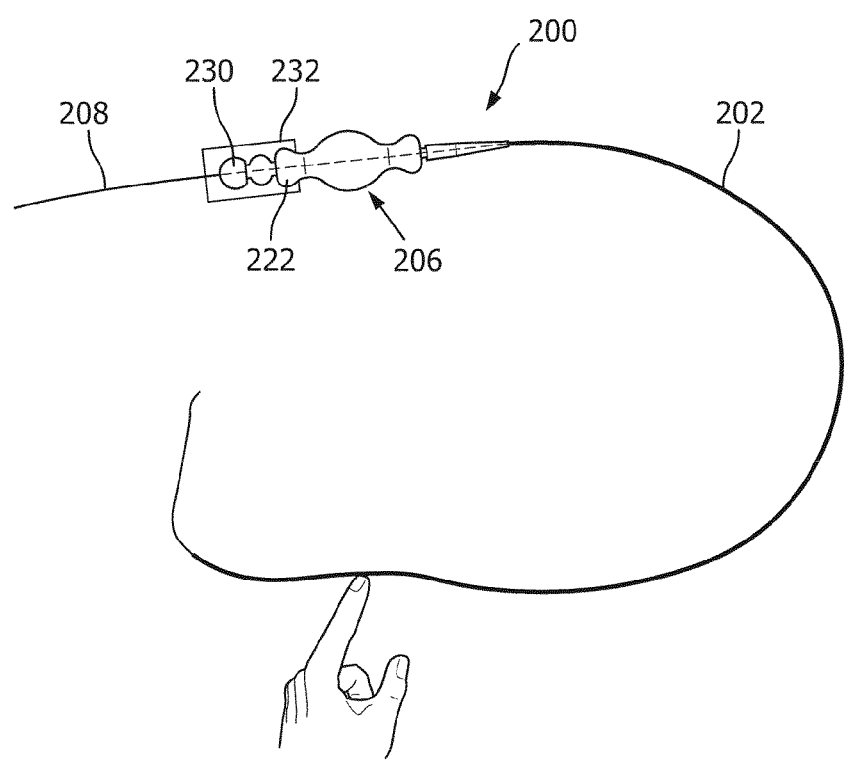
FIG. 3 is a schematic diagram showing a hub coupled to a catheter and a hemostatic valve and having a shape sensing guidewire running therethrough in accordance with one embodiment.

Referring to FIG. 3, a schematic diagram shows a shape sensed guidewire 208, a catheter 202 and a hub 206, which deforms the guidewire shape attached to the catheter 202 using the Luer lock system 200. Other features of the hub 206 may include a replicated female Luer 222 at the proximal portion of the hub 206 to permit other devices to mate thereon (as they would normally mate directly to a device). A hemostatic valve 230 or other device may be mounted to the female Luer lock 222 of the hub 206. A secondary lock 232 may be provided to capture the hub 206 and hemostatic valve 230 and prevent rotation or unwanted release between the devices. The secondary lock 232 may be split-half and may include securing features, like snaps, screws, fasteners, etc.

Figure 4:
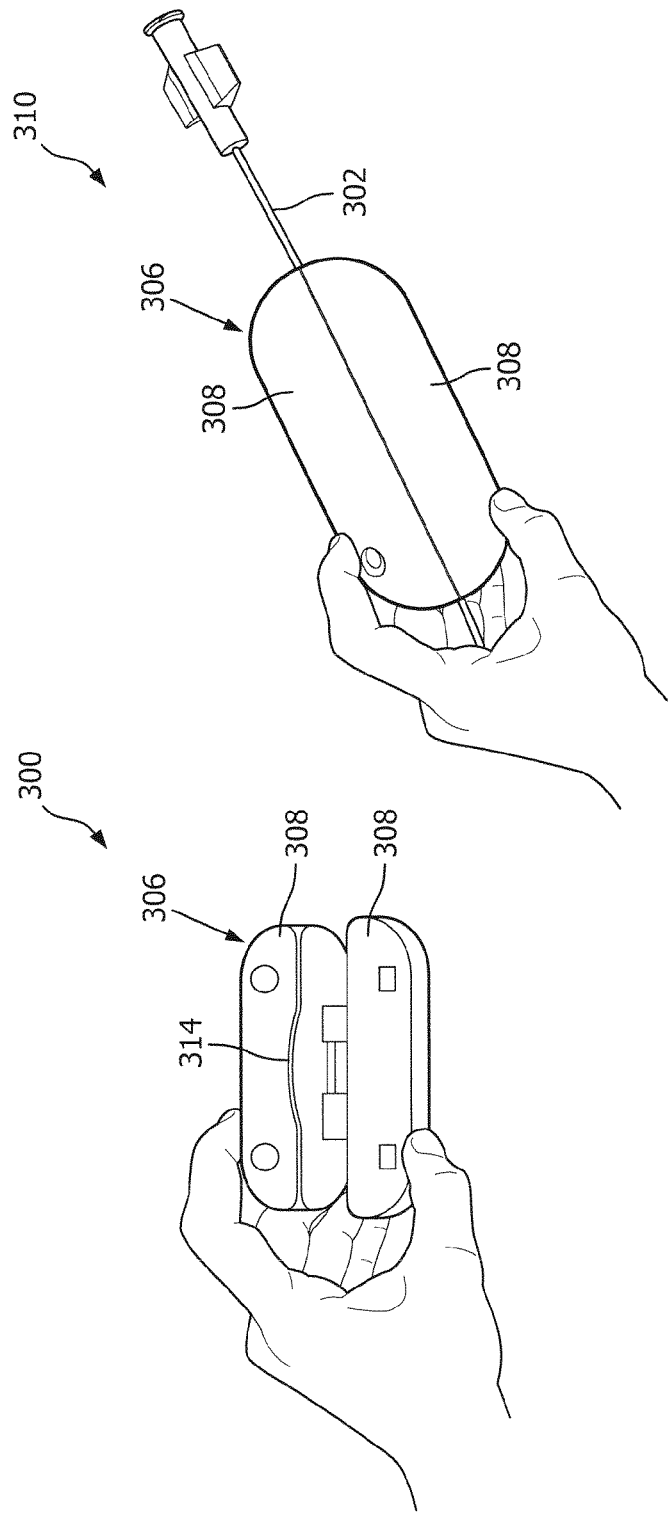
FIG. 4 shows images of a split half hub for an over-the-catheter design in accordance with one embodiment.

Referring to FIG. 4, in accordance with another embodiment, an over-catheter hub 306 suitable for use with smaller catheters includes an 'over-catheter' design. This may include split-half or clamshell portions 308 that a catheter 302 is placed into and then the over-catheter hub 306 is closed around the catheter 302. Alternatively, the catheter 302 may be passed through a lumen 314 in the over-catheter hub 306. The over-catheter design is desirable because it means that a guidewire (not shown) only passes through the catheter lumen. The over-catheter hub 306 does not add any additional lumen or components that interact with the guidewire. The lumen of the device (catheter 302) needs to be flexible enough to pass through the shape deformation in the over-catheter hub 306. This may be suitable for thinner, flexible devices like navigation catheters but may not be suitable for larger, stiffer devices, e.g., endograft deployment systems. In FIG. 4, instance 300 shows the over-catheter hub 306 with the clam-shell design in an open position showing a curved path for the lumen 314 in part of the clamshell portions 308. Instance 310 shows the over-catheter hub 306 clamped over the catheter 302. The catheter 302 includes a guidewire therein (not shown) and the guidewire includes a FORS™ system therein.

In another embodiment, a hemostatic valve (230, FIG. 3) may be employed with a mating male/female connection for a catheter. The valve is opened fully and a hub's distal portion may be inserted into the valve. Then, an outer component or secondary lock (232, FIG. 3) of the hub fastens around the valve to secure the hub in place. Multiple hub designs can be considered with varying paths for the guidewire. Examples of designs in addition to those already described are illustrated in FIG. 5.

Figure 5:
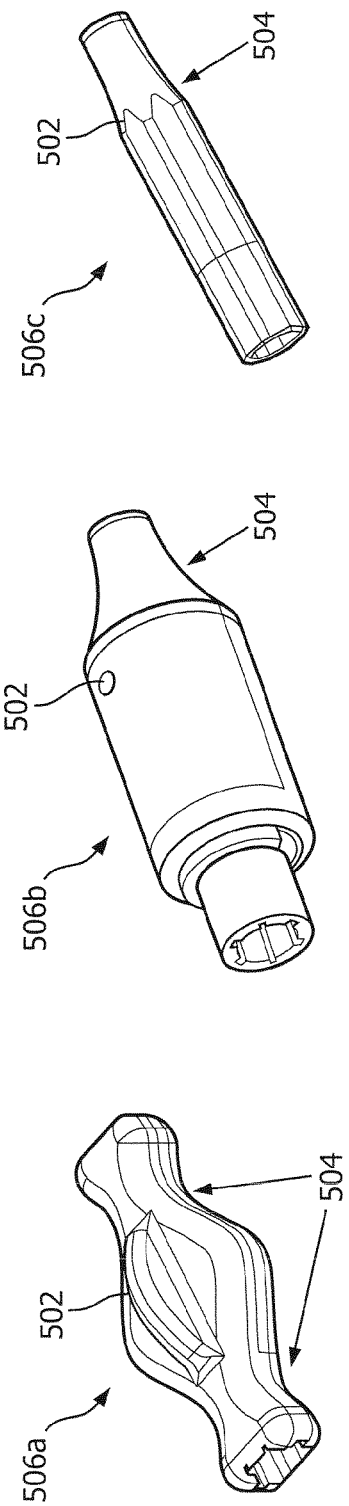
FIG. 5 shows a plurality of hubs having different shapes in accordance with illustrative embodiments.

Referring to FIG. 5, hub designs 506a, 506b, 506c (generally hub 506) may include many shapes and sizes. Different designs may include different profiles for guiding a FORS™ system within a guidewire. Features of the hubs in accordance with the present principles include some or all of the following features. An orientation feature 502, such as, a color marker, divot, or raised ridge feature that identifies the orientation of the device may be provided. This can enable the user to use the hub for rotational alignment or other registration functions. The hub 506 may include ergonomic features 504 to facilitate torqueing of a medical device 102 (FIG. 1). This could include a winged shape profile, a ridged profile, etc. to give users a better grip. A low-friction lumen or path (PTFE coated, hydrophilic coated, etc.) may be provided to minimize the effect on the guidewire.

Figure 6:
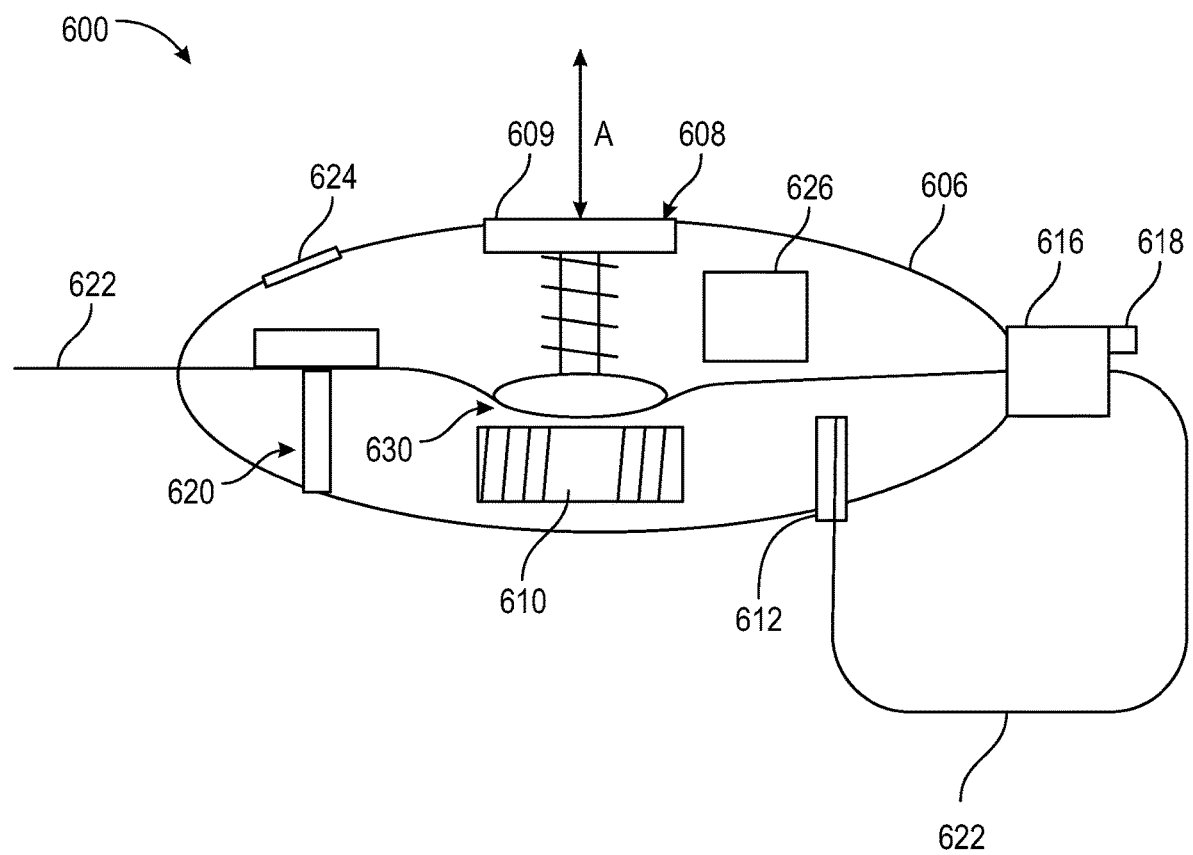
FIG. 6 is a cross-sectional view of a hub showing different features in accordance with illustrative embodiments.

Referring to FIG. 6, a hub 600 is schematically shown in accordance with one illustrative embodiment. The hub 600 includes a hub body 606, which may include a solid design, a split half design, etc. The hub body 606 includes an attachment feature 616 as described above, such as a Luer lock, etc. In one embodiment, the hub body 606 provides a deformable path that includes a mechanism 608 for displacing the flexible instrument to form a profile in the hub body in the deformable path to impart a hub template, when the mechanism is in a first position, to distinguish a portion of the elongated flexible instrument within the hub in shape sensing data.

The hub body 606 may include a biasing component (mechanism 608) such as a spring returned button 609 to induce the shape deformation when needed. By moving a shape sensed guidewire 622 (or catheter or other device with the shape sensed guidewire 622) in accordance with arrow "A", and locking in position to maintain a shape profile 630, a reversible hub profile can be achieved. This is advantageous because it permits the shape sensed guidewire 622 to pass straight through when not triggered, thus reducing the friction on the shape sensed guidewire 622. However, shape measurements are only accurate/updated when the mechanism 608 is triggered. Although a shape within the hub is described, that shape could alternatively be provided by a heating coil or coils 610 to cause a temperature profile to induce axial strain in the optical shape sensing fiber within the guidewire. The hub body 606 may also include a permanent shaped path. Hub body 606 may include any combination of path changes (e.g., permanent, heated, reversible) to form a shape profile 630. The shape profile 630 results in a set hub profile in shape sensed data.

body 606 and placed within the registration feature 612. The user initiates registration in the software (registration device 144, FIG. 1), and the length of the device is computed using the known relationship between the template position and the registration feature 612.

In one embodiment, the hub body 606 includes a proximal Luer lock or other attachment feature 616 that is free to rotate and pivot to allow improved usability. In addition, the attachment feature 616 may include torque stops, locks or other features 618 to prevent removal if twisting in one direction but permit removal in the other direction.

The hub body 606 may include radio-opaque or other such features 624 to permit for registration of the hub in another imaging modality (e.g., fluoroscopy/x-ray, MRI, CT, ultrasound, etc.). This could also include a radio-opaque lumen to detect a hub template. A locking mechanism 620 may be included to capture the shape sensed guidewire 622 to the hub body 606 so that they no longer translate with respect to each other. The locking mechanism 620 may include a spring loaded pin, a screw, a latch, a snap, etc.

In another embodiment, the hub body 606 may be identified using an identifier 626, which may include a code, serial number, radiofrequency identifier (RFID) tag, microchip, etc. in the hub body 606 to identify its hub template from a database or other reference. The hub body 606 may identify itself through the use of a unique template that may be stored in the database.

The hubs in accordance with the present principles can operate with a large variety of devices. In addition to catheters, for example, hubs may be employed with endograft deployment devices, etc. Other devices that may be employed with the hubs can include sheaths, introducers, mitral clip delivery systems, mitral valve delivery systems, aortic valve delivery systems, therapeutic catheters, balloon catheters, ablation catheters, imaging catheters (intravascular ultrasound (IVUS), optical coherence tomography (OCT), etc.), infusion catheters, endoscopes, needles, etc. While the over-the-wire devices are described as being placed over shape sensed guidewires, the present principles are not limited to a guidewire as the shape sensed device. Instead, any flexible elongated device may be employed and any tool with a shape sensed fiber within it may be employed to infer a shape of another tool. Although a retrofit hub has been described, the hub could also be fully integrated into the design of the catheter or medical device (over-the wire device). All of the features remain the same, with the exception of the attachment mechanism that attaches to the medical device.

Figure 7:
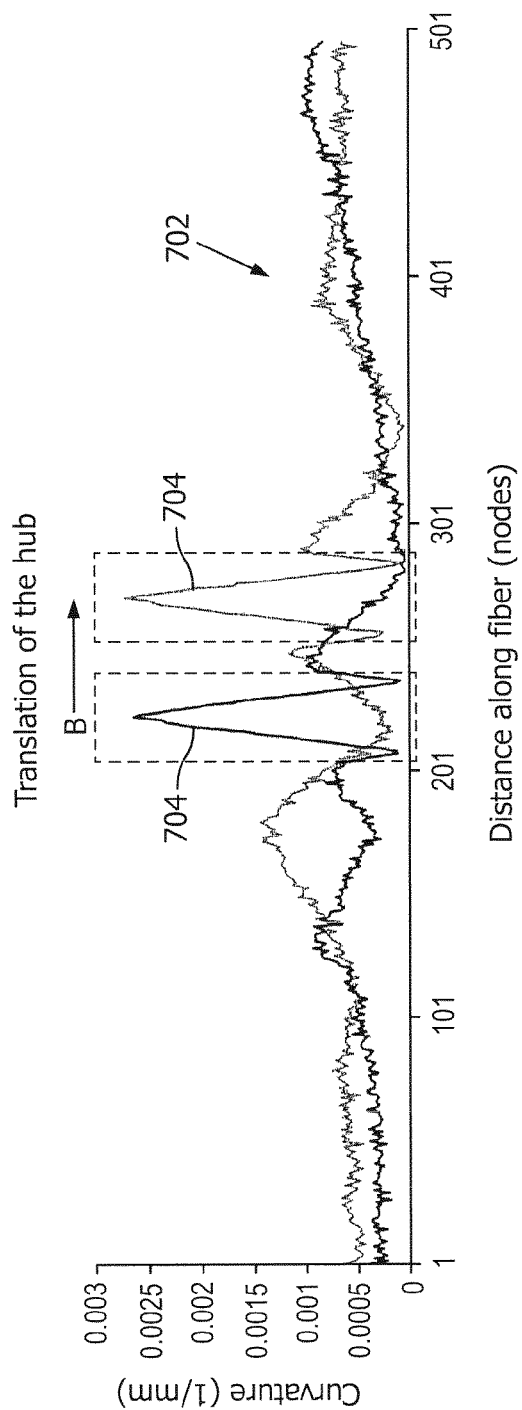
FIG. 7 is a graph showing shape sensing data with a hub template and showing the hub template shifting with movement of a hub in accordance with the present principles.

Referring to FIG. 7, a curvature plot or graph 702 showing curvature (1/mm) versus distance along a fiber (nodes) is shown. The plot or graph 702 shows a hub that has been translated from left to right as indicated by arrow "B" in two time period plots. A hub template 704 of the hub is shown being translated. For a hub to be used for longitudinal encoding, the hub template 704 of the hub curvature (or other shape profile) needs to be used to match against the guidewire curvature (or other shape profile). This hub template 704 can be derived in plurality of ways. These may include being selected by a user from a database of stored templates by entering an identifier that is written on the hub or hub packaging. In another example, the hub template 704 may be identified using a radiofrequency identifier (RFID) tag in the hub to identify its template from a database. In another example, the hub template 704 may be identified using a microchip in the hub that stores the hub template 704 completely.

A search algorithm may be employed that looks at shape sensed data along the shape sensed device and identifies the hub template 704 from within the shape data. This could be done fully automatically (e.g., a search algorithm can look along a straight guidewire and find the most likely hub candidate), with user input to confirm the automatically detected hub, or to limit the search range to find the hub, or to position the hub in two different locations (to help the algorithm find the thing that changed). This could also be done with full user input to select the hub from the shape, with x-ray (or other imaging such as optical, ultrasound, MRI, etc.) to image the hub and then detect the path, etc. The full template can be detected, or a pattern-matching algorithm could match the x-ray view of the hub to potential template matches in a database.

The hub template 704 may take on any usable shape including 2D or 3D profiles. The hub template 704 needs to be distinguishable from other shape sensing data. The use of an attachable hub is provided to cause the shape deformation of a shape sensed guidewire or tool through the visual shape representation of a device that is not enabled with shape sensing but that is being used with the shape sensed tool. This permits any commercial catheter (manual or robotic), deployment system, sheath, or other such device to be navigated using a shape sensed guidewire (or other tool). This may be applied to a plurality of useful applications, such as, e.g., vascular (catheters, sheaths, deployment systems, etc.), endoluminal (endoscopes), orthopedic (k-wires and screwdrivers) as well as non-medical applications and also applies to both manual and robotic manipulation of such devices.

Figure 8:
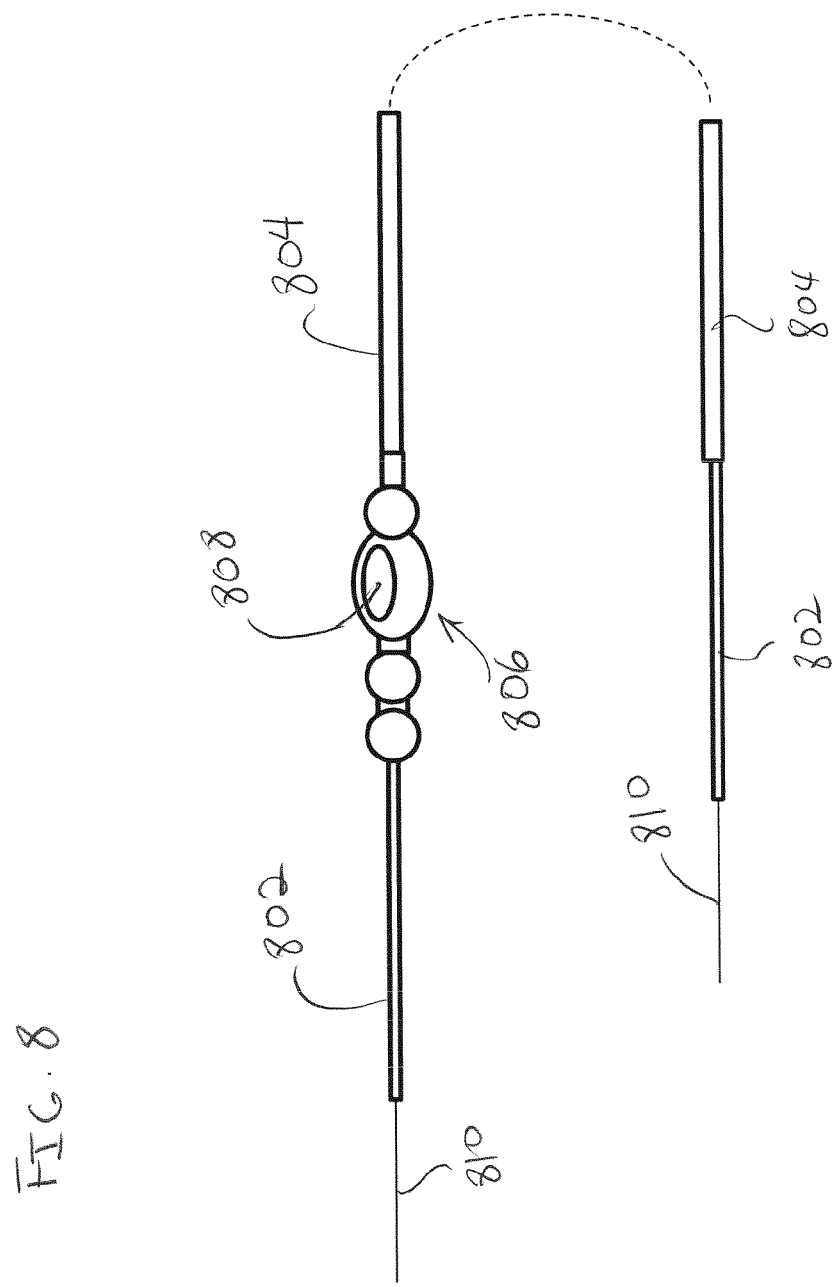
FIG. 8 is a diagram showing a dynamic hub with a deformable mechanism for setting a position of a shape sensed flexible instrument to infer a position/orientation of a deployable device in accordance with one embodiment.

Referring to FIG. 8, in accordance with one embodiment, a shape-sensed guidewire 802 is included in a catheter 804 with a hub 806. The hub 806 includes a deformable mechanism 808 (or switch) to deform a guidewire shape attached to the catheter 804 via a Luer lock or other device. If the catheter 804 (or other device) is employed over the shape-sensed guidewire 802, the guidewire shape also defines the catheter shape for the length over which the catheter 804 overlaps the shape-sensed guidewire 802. To properly define the position of the catheter 804, a relationship between the catheter 804 and the shape-sensed guidewire 802 needs to be known. This can be achieved by having the shape-sensed guidewire 802 with a FORS™ fiber or fibers 810 take on a specific shape, curvature, or strain profile at a specific position along the catheter 804. One way to induce such a shape, curvature or strain profile is to use the hub 806.

In some cases, it is not acceptable to have the hub 806 always maintain its effect on the shape. Thus, a dynamic version of the hub 806 can be employed that can selectively turn on and off its effect on an optical fiber employed in the shape-sensed guidewire 802. This permits any commercial catheter, deployment system, sheath, or other device to be navigated using the shape-sensed guidewire 802. The hub 806 can be employed with a back-loadable shape-sensed guidewire 802. The hub 806 is employed to create a shape deformation in the shape-sensed guidewire 802 that can be used for longitudinal registration. The hub 806 has a feature to enable turning on/off a curvature template. The hub 806 should be simple to switch between on/off states by an operator (e.g., while wearing surgical gloves, etc.). In addition, when the hub 806 is turned 'on', the hub 806 needs to create a reproducible change in the shape sensed guidewire 802.

The hub 806 is selectively interactable with the shape-sensed guidewire 802. For example, the hub 806 may introduce additional friction that could impact manipulation of the shape-sensed guidewire 802. In this case, the user may want to have the hub 806 in a disabled state during gross manipulations and then turn on the hub 806 for finer device manipulations. In the case of a FORS™-enabled back-loadable shape-sensed guidewire 802, there may be a region at a proximal end of the shape-sensed guidewire 802 that is completely rigid (due to optical components). If the hub 806 employs a curve or non-straight shape template then the hub 806 may be disabled when the stiff proximal section of the shape-sensed guidewire 802 passes through the hub 806.

The hub 806 is used to create shape deformation in the shape-sensed guidewire 802 be deflecting or pressing the mechanism 808 to provide a change in the fiber 810 to be used for longitudinal registration. The hub 806 has a feature or mechanism 808 to enable turning on/off a curvature template. The hub 806 is easily switched between on/off states by the operator (e.g., while wearing surgical gloves) or may be controlled remotely to create a reproducible template change in the shape sensed guidewire 802.

Figure 9A:
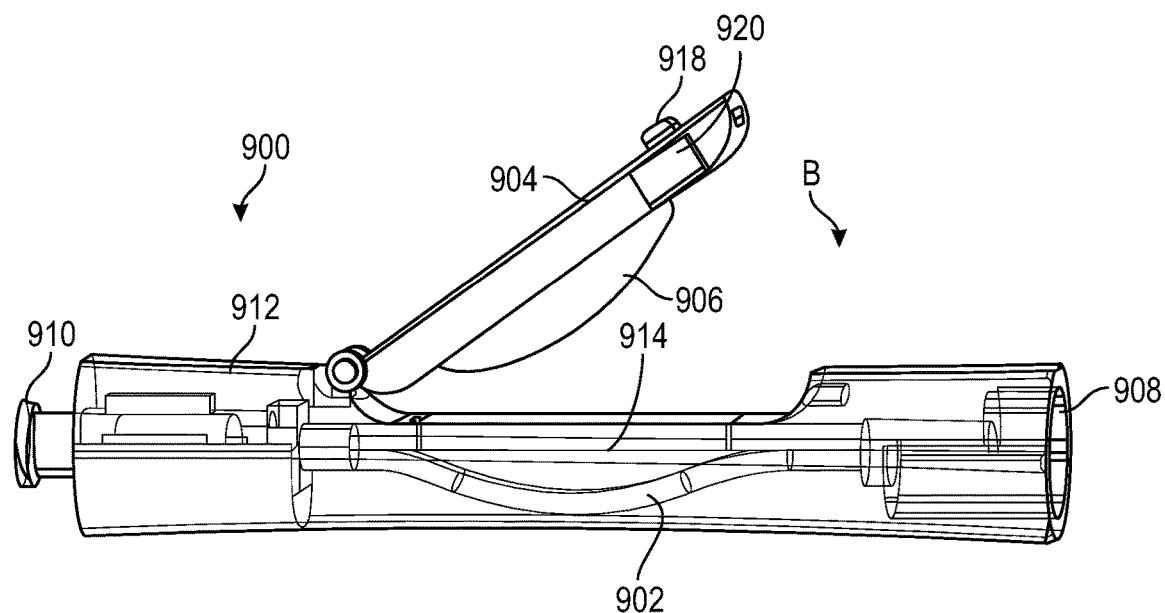
FIGS. 9A and 9B is a transparent side view showing a hub with a lever mechanism in an open position and a closed position to adjust a shape sensed flexible instrument in accordance with one embodiment.
Figure 9B:
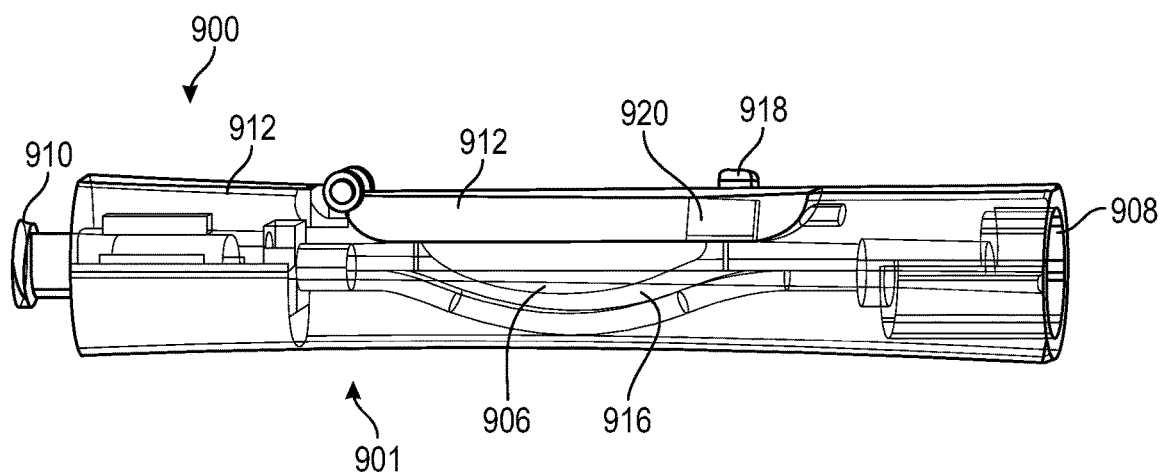
Figure 10C:
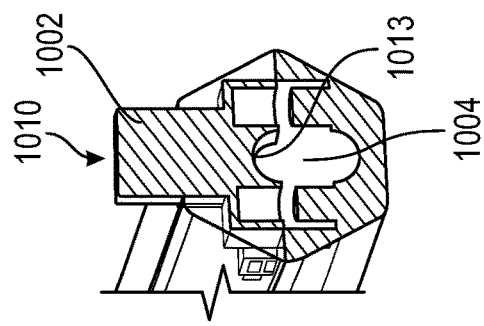
FIGS. 10A, 10B, 10C and 10D are transparent side views with corresponding cross-sectional views showing a hub with a push button mechanism in an open position and a closed position to adjust a shape sensed flexible instrument in accordance with another embodiment.
Figure 10D:
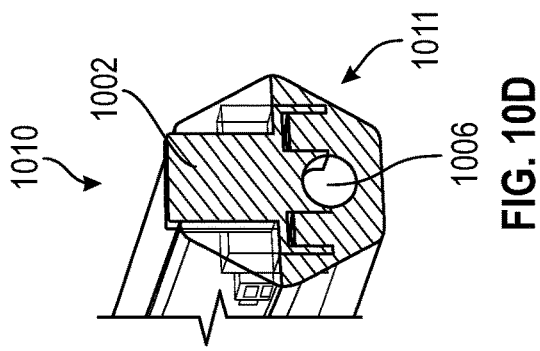
Figure 10A:
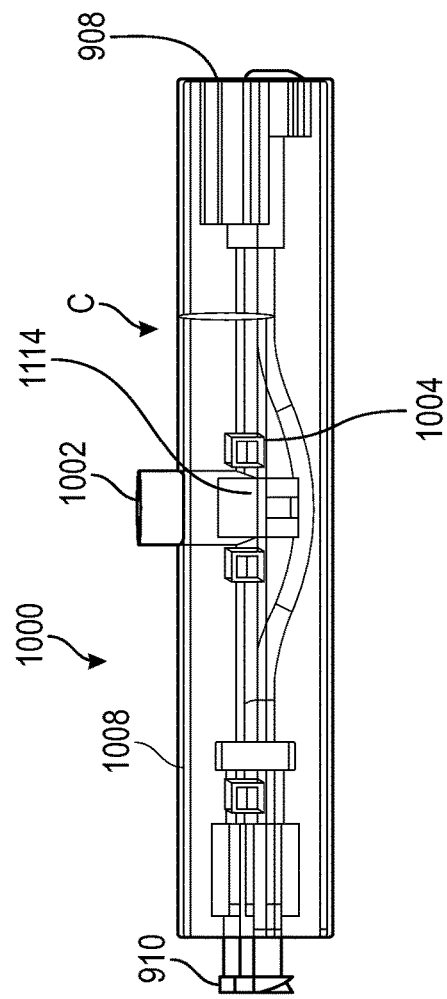
Figure 10B:
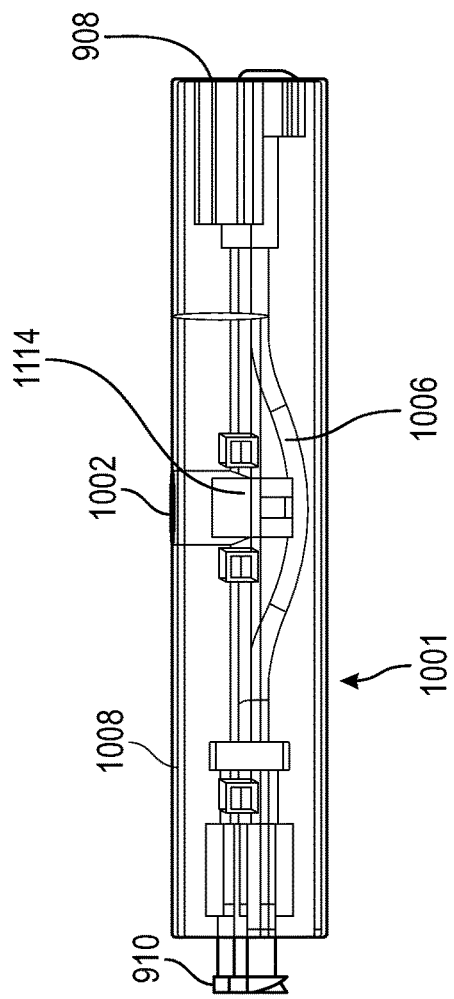

Referring to FIGS. 9A and 9B, a lever or latching lever hub 912 is shown in an open position 900 and a closed position 901. The latching lever hub 912 includes a hinged lever 904 having an engagement portion 906. The latching lever hub 912 includes Luer lock connections 910 and 908 (or other standard connections) for engaging or connecting the hub to a catheter or other device. A shape sensing fiber (shape-sensing guidewire) is threaded through or otherwise loaded into the latching lever hub 912. When the lever 904 is open, in open position 900, the fiber is disposed on a straight path 914 through the latching lever hub 912. When the lever 904 is in a closed position, the fiber is disposed on a curved path 902 through the latching lever hub 912. The hinged lever 904 can now be moved in the direction of arrow "B" so that the engagement portion engages and moves the fiber to a curved path 916 as shown in the closed position 901.

A curved template is provided with curved path 916 while also allowing for the straight path 914 as a default. However, the curved path 916 may be the default in some embodiments. When the hinged lever 904 is pressed, the template curvature is forced down onto the guidewire or fiber inside the latching lever hub 912 so that the template is introduced to the sensing data signal. A latch or latching mechanism 918 (e.g., a clip, hook, etc.) may be employed to hold the hinged lever 904 in the closed position 901, thereby not requiring the user to constantly hold the hinged lever 904 in the closed position 901. A release 920 may also be employed that can be depressed to release the hinged lever 904 from the closed position 901. Other latching mechanisms or release mechanisms may also be employed.

Referring to FIGS. 10A, 10B, 10C and 10D, in another embodiment, a pushbutton or latching pushbutton hub 1008 is shown in an open position 1000 and a closed position 1001. The pushbutton or latching push bottom hub 1008 includes a push button 1002 having an engagement portion 1012 shown in a cross-section 1010 of the push button 1002. The pushbutton or latching push bottom hub 1008 includes Luer lock connections 910 and 908 for engaging or connecting the pushbutton or latching push bottom hub 1008 to a catheter or other device. A shape sensing fiber (shape-sensing guidewire) is threaded through or otherwise loaded into the pushbutton or latching push bottom hub 1008. When the push button 1002 is retracted in the open position 1000, the fiber is disposed on a straight path 1004 through the pushbutton or latching push bottom hub 1008. The push button 1002 can now be moved in the direction of arrow "C" so that the engagement portion engages and moves the fiber to a curved path 1006 as shown in the closed position 1001 and a cross-section 1011 of the closed position.

A curved template is provided with curved path 1006 while also allowing for the straight path 1004 as a default. However, the curved path 1006 may be the default in some embodiments. When the push button 1002 is pressed, the template curvature is forced down onto the guidewire or fiber inside the pushbutton or latching push bottom hub 1008 so that the template is introduced. A latch or latching mechanism 1114 (e.g., a clip, hook, etc.) may be employed to hold the push button 1002 in the closed position 1001, thereby not requiring the user to constantly hold the push button 1002 in the closed position 1001. A release may also be employed that can be depressed to release the push button 1002 from the closed position 1001. Other latching mechanisms or release mechanisms may also be employed.

Springs or a biasing device may be employed to force the push button 1002 into its default position, e.g., to permit the guidewire to pass through unimpeded. The pushbutton or latching push bottom hub 1008 can be sealed at all times.

Figure 11:
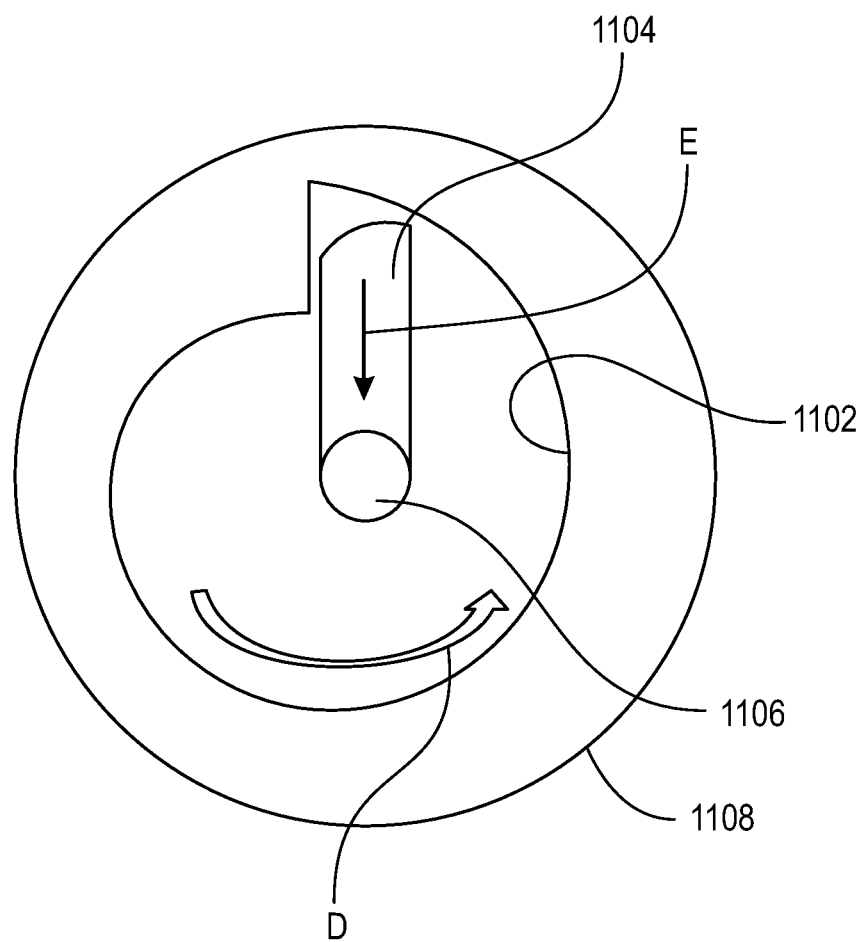
FIG. 11 is a cross-sectional view showing a cam, cam follower and knob for adjusting a shape sensed instrument in accordance with another embodiment.
Figure 12A:
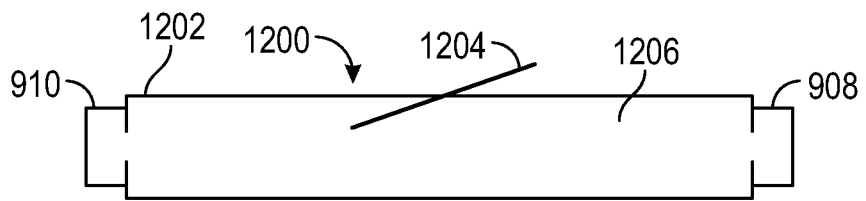
Figure 12C:
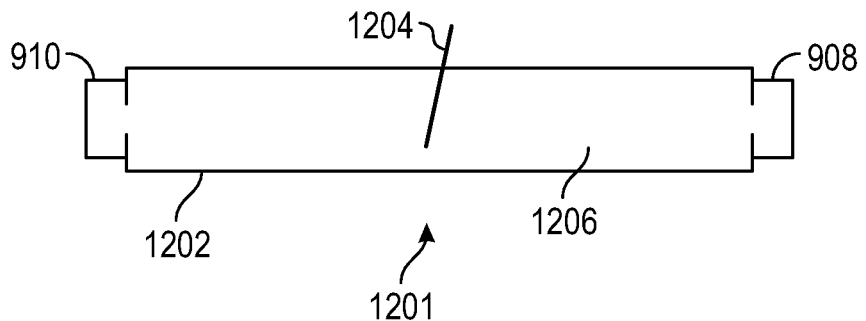

Referring to FIG. 11, a cross-section of cam 1102 and a cam follower mechanism 1104 to introduce a template are illustratively shown in accordance with another embodiment. As a knob 1108 is turned in the direction of arrow "D", the cam follower mechanism 1104 is forced down in the direction of arrow "E" onto a guidewire 1106. The cam follower mechanism 1104 follows the contour of a surface of the cam 1102.

In this embodiment, the template is applied directly to the guidewire 1106 as a rotational input using the cam 1102. The knob 1108 can be added to any hub. As the knob 1108 is turned, the cam 1102 rotates and moves the cam follower mechanism 1104, which in turn forces the template curvature onto the guidewire 1106. This permits variable templates and may impart different levels of curvature, e.g., the more the knob 1108 is turned, the more curvature is applied to the guidewire 1106.

Different types of cams may be employed. For example, a barrel cam may be employed with the cam follower attached to a bent lever. As the barrel cam is rotated, the lever arm moves up and down, thereby introducing the template. One advantage of the cam embodiments includes providing a progressive amount of curvature that can be applied depending on the amount of rotation. Stiffer guidewires may take on less curvature in a body, and may also be more sensitive to curvature in the hub (thereby inducing more friction during navigation). Different guidewires could have different pre-set rotations corresponding to differing amounts of curvature, depending on their stiffness.

Referring to FIGS. 12A, 12B, 12C and 12D, in another embodiment, a lever 1204 may be employed to deflect a fiber or guidewire 1206 in a hub 1202. In position 1200, the lever 1204 is in a neutral state and is not engaged with fiber or guidewire 1206. In position 1201, the lever 1204 is rotated about a pivot point to engage the fiber or guidewire 1206. The lever 1204 can be employed with the fiber or guidewire 1206 to induce a deformation/offset at a point in the hub 1202 in position 1201. This reduces friction because only a single point of contact is made with the fiber or guidewire 1206.

Figure 13A:
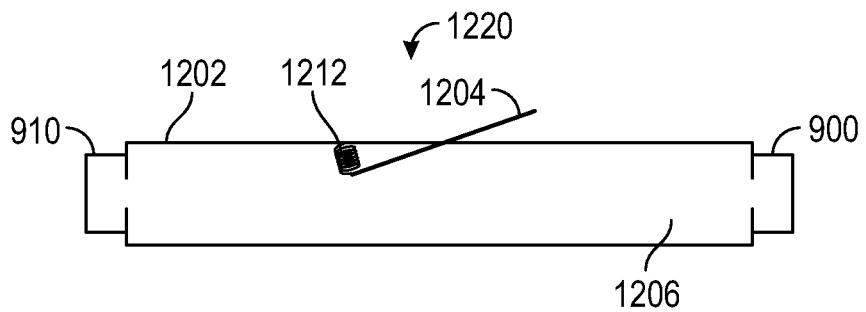
FIG. 13 is a transparent side view showing a hub with a biased lever mechanism in an engaged position and in an unengaged position to adjust a shape sensed flexible instrument in accordance with another embodiment.
Figure 13B:
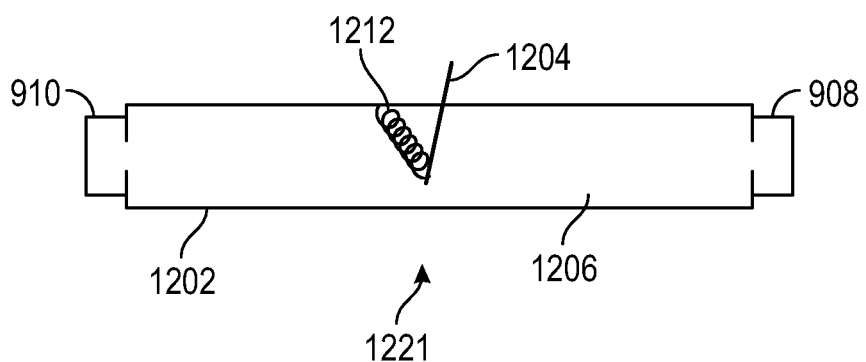

Referring to FIG. 13, in another embodiment, the lever 1204 may be employed to deflect the fiber or guidewire 1206 in the hub 1202 using a biasing member or spring 1212. In position 1220, the lever 1204 is in a retracted state maintained by the spring 1212 and is not engaged with fiber or guidewire 1206. In position 1221, the lever 1204 is rotated about a pivot point to engage the fiber or guidewire 1206. The lever 1204 can be employed with the fiber or guidewire 1206 to induce a deformation/offset at a point in the hub 1202 in position 1221. This reduces friction because only a single point of contact is made with the fiber or guidewire 1206. The bias of spring 1212 causes the lever to return to position 1220 when released. The lever 1204 can be secured in either state using mechanical elements.

Alternatively, in other embodiments, the guidewire may be disposed in a tube (fiber or guidewire 1206) that deflects the guidewire therein when engaged with the lever 1204 (or any other element as described herein). The tube could protect the guidewire and/or further reduce friction. In addition, the spring 1212 could be used to create a preferred state. For example, that the hub 1202 may have as a default, the lever 1204 applied, and the user depresses the lever 1204 to remove the curvature.

Figure 14A:
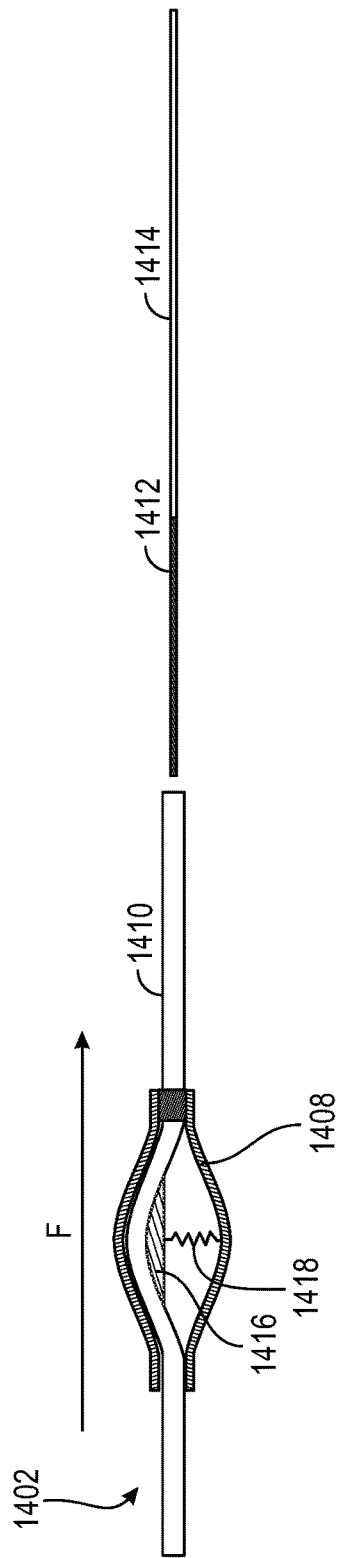
FIGS. 14A, 14B and 14C shows a progression of views of a biased hub being loaded on a guidewire in accordance with another embodiment.
Figure 14B:
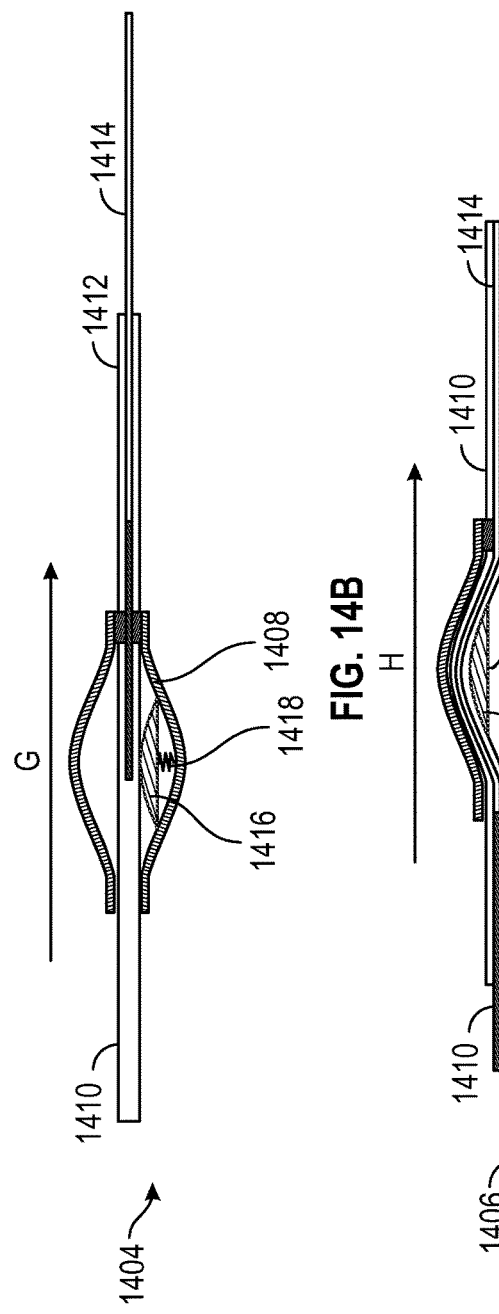
Figure 14C:
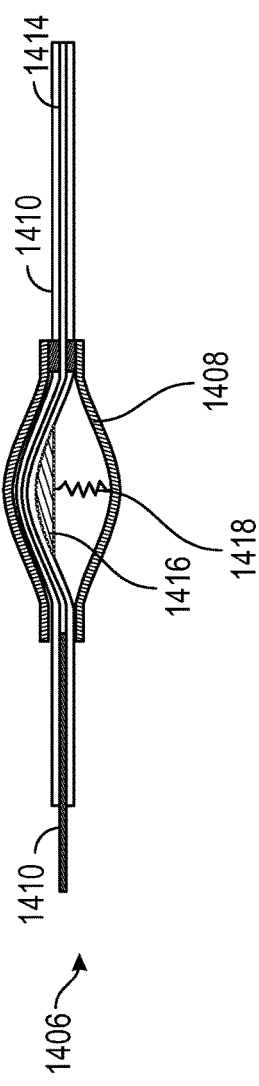

Referring to FIGS. 14A, 14B and 14C, a hub 1408 is shown in three positions 1402, 1404, and 1406 along a guidewire 1414. In position 1402, the hub 1408 includes an engagement portion 1416 having a biasing device 1418, such as, e.g., a spring or other mechanism for applying a force against a catheter 1410 or other device. The guidewire 1414 includes a stiff proximal portion 1412 that leads the guidewire 1414 and will be passed first into the catheter 1410 and the hub 1408 in the direction of arrow "F".

In position 1404, instead of having a fixed curvature in the hub 1408, the biasing device 1418 pushes a curved part onto the catheter 1410 to create a desired curve. When the stiff proximal portion 1412 of the guidewire 1414 enters the hub 1408, the stiff proximal portion 1412 enters the hub 1408 and displaces the biasing device 1418 to permit passage of the stiff proximal portion 1412. The stiff proximal portion 1412 pushes the engagement portion 1416 (curved portion) inside the hub to straighten it when the hub 1408 is moved in the direction of arrow "G".

In position 1406, when the stiff proximal portion 1412 of the guidewire 1414 is advanced (in the direction of arrow "H") passed the hub 1408, the biasing device 1418 pushes the catheter 1410 and the guidewire 1414 into a desired curve or template. The biasing device 1418 may include a spring, a manual force, etc. and may be applied at different positions in the hub 1408.

Figure 15A:
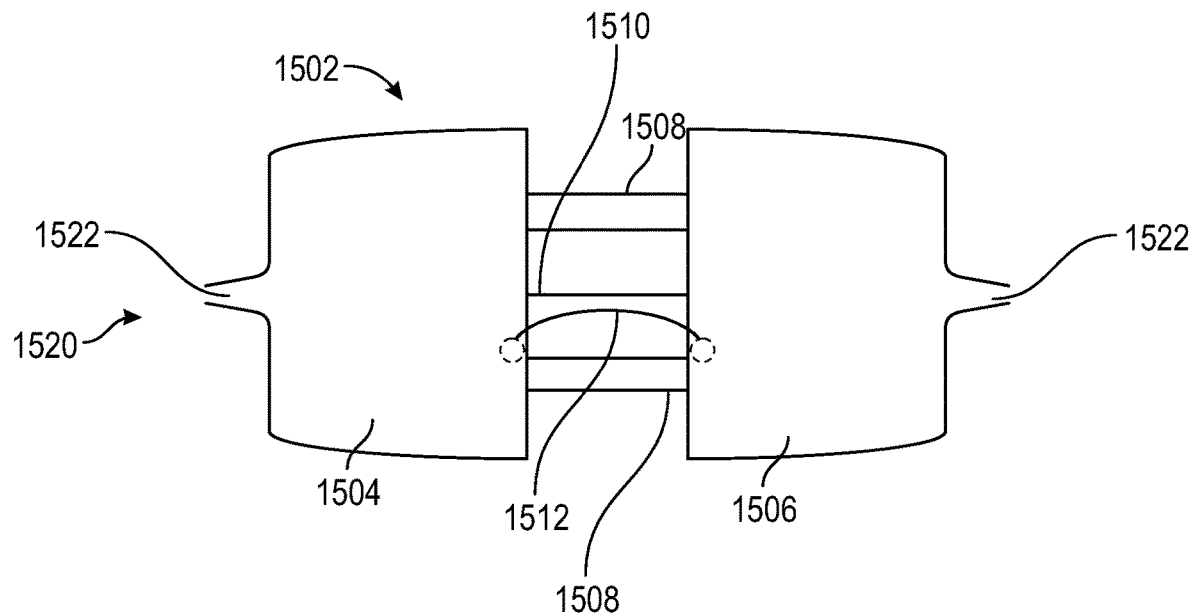
FIG. 15 is a side view showing a compression hub in an open position and a closed position to adjust a shape sensed flexible instrument in accordance with another embodiment.
Figure 15B:
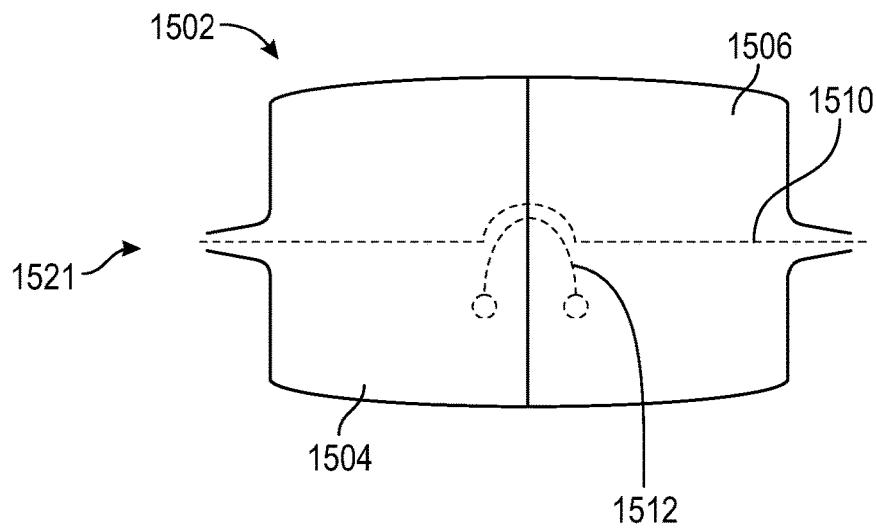

Referring to FIG. 15, a compressing hub 1502 is depicted in accordance with another embodiment. The compressing hub 1502 includes an open position 1520 where a shape-enabled guidewire 1510 or FORS™ fiber is inserted through open ends 1522. The shape-enabled guidewire 1510 may be placed in a protective tube. A guiding feature 1512 is located adjacent to the tube/guidewire/fiber 1510. The compressing hub 1502 may include separable portions 1504 and 1506 that are separated in the open position 1520. The separable portions 1504 and 1506 may be guided using guides 1508 or other mechanical features.

When the separable portions 1504 and 1506 are closed in position 1521 the shape-enabled guidewire 1510 is compressed and forms a curved shape due to the path-length change. The guiding feature 1512 may be bowed to ensure a reproducible template.

In all designs, software (optical sensing module 122, FIG. 1) may be employed to detect when the hub template is present by looking for a match of a shape where the match is computed to be better than a threshold value. The visualization of the device would only happen once the hub was 'on' and the template match was detected. Alternatively, if this is not sensitive enough, the hub could have an additional feature to give input as to its on/off state. This may include an electronic signal, a mechanical switch, an RF signal or any other signal or assisting method known in the art. For example, when the hub has a lever engaged, halves closed, pressure applied, a signal is generated and the visualization of the shape is checked for by the optical sensing module 122 (FIG. 1).

Throughout this disclosure the guidewires described included shape sensing fiber or fibers. It should be understood that the present principles are not limited to guidewires as the shape sensed devices. Any tool with a shape sensed fiber associated therewith may be employed to infer a shape of another tool. The hubs/dynamic hubs described herein may include retrofit hubs that slide over devices to provide a template. In addition, the hub may also be fully integrated into a catheter (or medical device). The features described remain the same for fully integrated hubs, but with attachment mechanisms adjusted depending on the device having the hub thereon.

In addition, the shapes depicted in some of the embodiments show a simple curve for illustrative purposes. It should be understood that the curve(s) may be more complex having multiple inflections, different cusps or arcuate shapes, multiple shapes, etc. to provide the templates for device or position identification.

The hubs and dynamic hubs described herein may be employed with any commercial catheter (manual or robotic), deployment system, sheath, or other such device to be navigated using a shape sensed guidewire or other device for any applications such as, e.g., vascular (catheters, sheaths, deployment systems, etc.), endoluminal (endoscopes), orthopedic (k-wires and screwdrivers) as well as non-medical applications.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for a hub for device navigation with an optical shape sensed guidewire (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A hub for optical shape sensing reference, comprising:
a hub body configured to receive an elongated flexible instrument with a shape sensing system coupled to the flexible instrument within a path formed in the hub body;
a profile formed in the hub body in the path to impart a hub template configured to distinguish a portion of the elongated flexible instrument within the hub body in shape sensing data;
an attachment mechanism formed on the hub body to detachably connect the hub body to a deployable instrument such that a change in a position of the hub body indicates a corresponding change in the deployable instrument;
a processor; and
a memory that stores instructions, which when executed by the processor, cause the processor to identify a position of the hub template in the shape sensing data to account for a position of the hub and the deployable instrument during deployment in a medical procedure.

2. The hub as recited in claim 1, wherein the elongated flexible instrument includes a guidewire and the shape sensing system is disposed within the guidewire.

3. The hub as recited in claim 1, wherein the profile includes a two-dimensional or three-dimensional off-axis shape or strain.

4. The hub as recited in claim 1, wherein the deployable instrument includes one of a catheter, a sheath, a balloon and an implantable device, and the hub connects to the deployable instrument.

5. The hub as recited in claim 1, wherein the attachment mechanism includes a Luer lock.

6. The hub as recited in claim 1, wherein the attachment mechanism includes a hemostatic valve attachment.

7. The hub as recited in claim 1, wherein the hub body includes split-half portions to receive at least one of the deployable instrument and/or the elongated flexible instrument.

8. The hub as recited in claim 1, wherein the hub body includes at least one of radiopaque markings and surface features configured to align, register and/or view the hub body in medical images.

9. The hub as recited in claim 1, wherein the hub template is imparted by one of: a biased portion, a shape of the profile, and a temperature changing device.

10. The hub as recited in claim 1, wherein the elongated flexible instrument is disposed within a lumen of an over the wire device that is not shape sense enabled and the hub template is configured to register the over the wire device to the elongated flexible instrument.

11. A system for optical shape sensing, comprising:
a hub body configured to receive an elongated flexible instrument with an optical shape sensing system coupled to the flexible instrument within a path formed in the hub body;
a profile formed in the hub body in the path to impart a hub template configured to distinguish a portion of the elongated flexible instrument within the hub in shape sensing data;
an attachment mechanism formed on the hub body to detachably connect the hub body to a deployable instrument;
a processor; and
a memory that stores instructions, which when executed by the processor, cause the processor to: interpret the shape sensing data to identify the hub template in the shape sensing data to account for a position of the hub and the deployable instrument during deployment in a medical procedure; and identify a position of the hub template is in the shape sensing data to account for a position of the hub and the deployable instrument during deployment in a medical procedure.

12. The system as recited in claim 11, wherein the elongated flexible instrument is disposed within a lumen of an over the wire device that is not shape sense enabled and the hub template is configured to register the over the wire device to the elongated flexible instrument.

13. A system for optical shape sensing, comprising:
a hub body configured to receive an elongated flexible instrument with an optical shape sensing system coupled to the flexible instrument within a deformable path formed in the hub body;
the deformable path includes a mechanism for displacing the flexible instrument to form a profile in the hub body in the deformable path to impart a hub template, when the mechanism is in a first position, to distinguish a portion of the flexible instrument within the hub in shape sensing data;

an attachment mechanism formed on the hub body to detachably connect the hub body to a deployable instrument;

a processor; and a memory that stores instructions, which when executed by the processor causes the processor to identify a position of the hub template in the shape sensing data to account for a position of the hub and the deployable instrument during deployment in a medical procedure, wherein one end of the deformable path formed in the hub body is configured to lead to a lumen of the deployable device via a connection between the hub body and the deployable device.

* * * * *